United States Patent [19]
Stelzer

[11] Patent Number: 6,046,351
[45] Date of Patent: Apr. 4, 2000

[54] PROCESS FOR PREPARING RACEMIC PHENETHYLAMINES

[75] Inventor: Uwe Stelzer, Burscheid, Germany

[73] Assignee: Bayer Aktiengesellschaft, Leverkusen, Germany

[21] Appl. No.: 09/230,232

[22] PCT Filed: Jul. 11, 1997

[86] PCT No.: PCT/EP97/03691

§ 371 Date: Jan. 19, 1999

§ 102(e) Date: Jan. 19, 1999

[87] PCT Pub. No.: WO98/03465

PCT Pub. Date: Jan. 29, 1998

[30] Foreign Application Priority Data

Jul. 23, 1996 [DE] Germany .................. 196 29 692

[51] Int. Cl.$^7$ .................. C07C 305/04; C07C 313/12; C07C 255/50; C07C 211/03
[52] U.S. Cl. .................. 558/55; 558/61; 558/418; 564/381
[58] Field of Search .................. 558/55, 61, 418; 564/381

[56] References Cited

U.S. PATENT DOCUMENTS

| | | | |
|---|---|---|---|
| 4,988,734 | 1/1991 | Kraatz et al. .................. | 514/624 |
| 5,183,939 | 2/1993 | Jansen et al. .................. | 564/302 |
| 5,668,140 | 9/1997 | Schaper et al. .................. | 514/269 |
| 5,728,876 | 3/1998 | Balkenhohl et al. .................. | 564/136 |

FOREIGN PATENT DOCUMENTS 0 264 217  10/1987  European Pat. Off. .
0 453 137  10/1991  European Pat. Off. .

OTHER PUBLICATIONS

JP Abstracts of Japan, vol. 95, No. 010 & JP 07188120 Jul. 25, 1995.

JP Abstracts of Japan, vol. 96, No. 005 & JP 08027073 Jan. 30, 1996.

*Primary Examiner*—Johann Richter
*Assistant Examiner*—Joseph Murray
*Attorney, Agent, or Firm*—Joseph C. Gil; Carol Marmo

[57] ABSTRACT

The invention concerns a novel process for preparing racemic phenethylamines of formula (I)

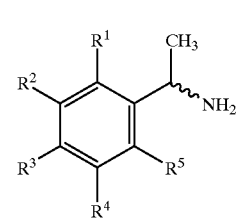

(I)

in which $R^1$, $R^2$, $R^3$, $R^4$ and $R^5$ have the meanings given in the description. According to this process: a) in a first step, optically active phenethylamines of formula (I*)

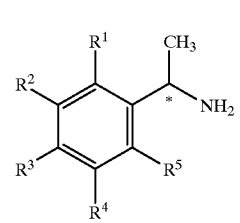

(I*)

are reacted with acetophenone derivatives of formula (II),

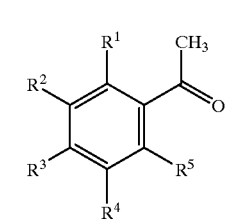

(II)

the optically active phenethylamine used and the acetophenone derivative used each being substituted in an identical manner in the phenyl part, optionally in the presence of a diluting agent and optionally in the presence of a catalyst; b) in a second step, the resultant optically active Schiff bases of formula (III*)

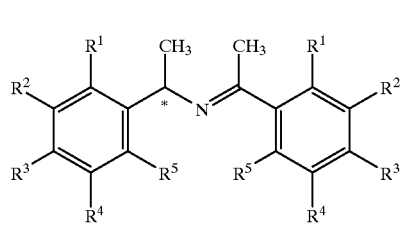

(III*)

are reacted with metallic hydroxides containing between 0.1 and 50 wt. % water; and c) in a third step, the resultant racemic Schiff bases are reacted with acids in the presence of water.

8 Claims, No Drawings

PROCESS FOR PREPARING RACEMIC PHENETHYLAMINES

TECHNICAL FIELD OF THE INVENTION

The present invention relates to a novel process for the preparation of known phenethylamines by racemization of cally active phenethylamines.

BACKGROUND OF THE INVENTION

Several processes for the preparation of optically active phenethylamines are already known (cf. EP-A 0 341 475). In these processes, the racemic starting materials are resolved into the individual enantiomers by adding auxiliary reagents. In order to make these known processes for racemate resolution economical, the enantiomers which are in each case undesired must be racemized again and returned to the cycle.

In this connection, several methods have already been described which are suitable for racemizing enantiomers of phenethylamines which are not required. For example, optically active phenethylamines can be converted into the corresponding racemates by treatment with alkoxides in the presence of dimethyl sulphoxide (cf. EP-A 0 489 682). The process does, however, have the disadvantage that the alkoxides which are used as auxiliary reagents are relatively costly.

In addition, it has already been disclosed that racemic phenethylamines can be prepared by reacting optically active phenethylamines with acetophenone derivatives, then racemizing the resulting optically active Schiff bases using potassium tert-butoxide, and cleaving the resulting racemic Schiff bases using acids (cf. JP-A 07-188 120 and Derwent Abstract No. 95-290 356/38). A disadvantage of this process, however, is that the yields of the desired racemates are not always satisfactory. It is also unfavourable that the racemization requires potassium tert-butoxide, which is expensive.

DETAILED DESCRIPTION OF THE INVENTION

It has now been found that racemic phenethylamines of the formula

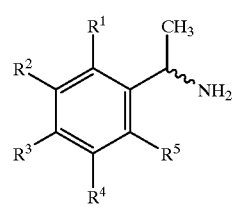

(I)

in which
$R^1$, $R^2$, $R^3$, $R^4$ and $R^5$ independently of one another are hydrogen, halogen, cyano, nitro, alkyl, alkoxy, alkylthio, alkylsulphinyl, alkylsulphonyl, dialkylamino, halogenoalkyl, halogenoalkoxy, halogenoalkylthio, halogenoalkylsulphinyl or halogenoalkylsulphonyl, are obtained when
a) in a first stage, optically active phenethylamines of the formula

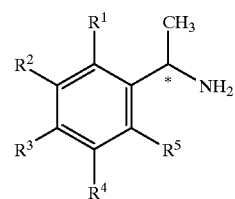

(I*)

in which
$R^1$, $R^2$, $R^3$, $R^4$ and $R^5$ are as defined above,
are reacted with acetophenone derivatives of the formula

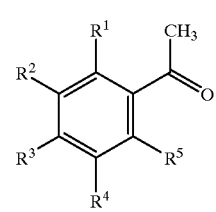

(II)

in which
$R^1$, $R^2$, $R^3$, $R^4$ and $R^5$ are as defined above,
the optically active phenethylamine used and the acetophenone derivative used each being identically substituted in the phenyl moiety,
optionally in the presence of a diluent and optionally in the presence of a catalyst,
b) then in a second stage, the resulting optically active Schiff bases of the formula

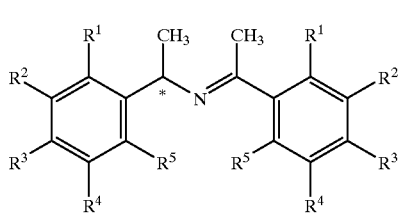

(III*)

in which
$R^1$, $R^2$, $R^3$, $R^4$ and $R^5$ are as defined above,
are reacted with metal hydroxides having a water content of between 0.1 and 50% by weight, optionally under a protective-gas atmosphere, and
c) in a third stage, the resulting racemic Schiff bases of the formula

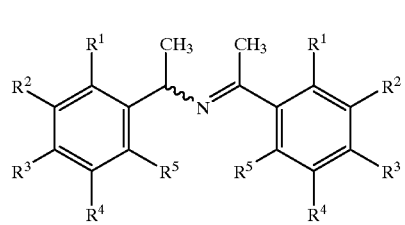

(III)

in which
$R^1$, $R^2$, $R^3$, $R^4$ and $R^5$ are as defined above, are reacted with acids in the presence of water.

To indicate optically active compounds, the chiral centre in the above formula and also in the text below is in each case marked by (*).

It is extremely surprising that racemic phenethylamines of the formula (I) can be prepared by the process according to the invention in higher yields than by the most similar previously described process in which optically active Schiff bases are racemized using potassium tert-butoxide. Moreover, on the basis of the previously disclosed prior art, it must be assumed that optically active phenethylamines of the formula (I*) are considerably decomposed when treated with hydrous metal hydroxides. Contrary to expectations, however, this is not the case.

The process according to the invention is distinguished by a number of advantages. For example, it permits the preparation, in very high yield, of racemic phenethylamines from undesired enantiomers which are inevitably produced during racemate resolutions. It is also favourable that both the (R)- and also (S)-enantiomers can be readily racemized to the same extent and that the substituents on the phenyl ring can be varied widely. It is also advantageous that the racemization is carried out using low-cost metal hydroxide. Finally, the carrying out of the reactions and isolation of the desired substances do not present any problems of any sort.

If (S)-1-(4-chloro-phenyl)-ethylamine and 4-chloracetophenone are used as starting materials, aqueous potassium hydroxide as racemization reagent, and aqueous hydrochloric acid for cleaving the racemic Schiff base, the progress of the process according to the invention may be illustrated by the following equation.

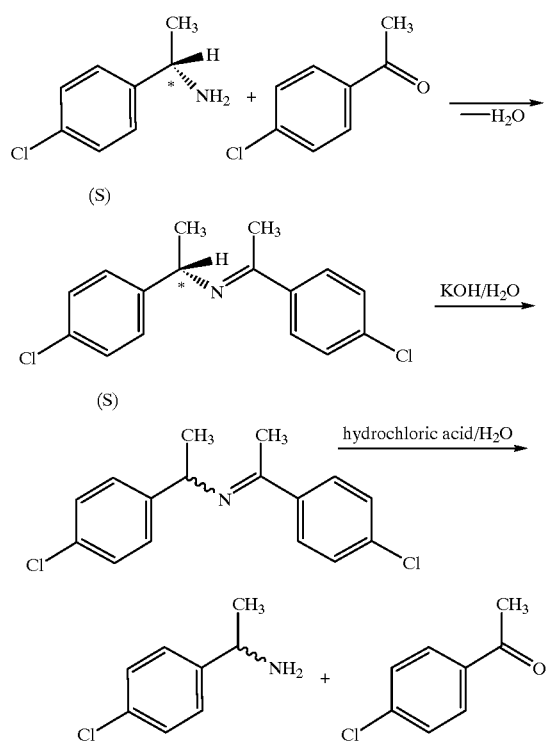

The optically active phenethylamines required as starting materials for carrying out the process according to the invention are generally defined by the formula (I*). The chiral centre can either have the (R)- or the (S)- configuration.

Preference is given to phenethylamines of the formula (I*), in which $R^1$, $R^2$, $R^3$, $R^4$ and $R^5$ independently of one another are hydrogen, fluorine, chlorine, bromine, cyano, nitro, alkyl having from 1 to 4 carbon atoms, alkoxy having 1 or 2 carbon atoms, alkylthio having 1 or 2 carbon atoms, alkylsulphinyl having 1 or 2 carbon atoms, alkylsulphonyl having 1 or 2 carbon atoms, dialkylamino having in each case 1 or 2 carbon atoms in the alkyl chains, halogenoalkyl having 1 or 2 carbon atoms and from 1 to 5 halogen atoms, halogenoalkoxy having 1 or 2 carbon atoms and from 1 to 5 halogen atoms, halogenoalkylthio having 1 or 2 carbon atoms and from 1 to 5 halogen atoms, halogenoalkylsulphinyl having 1 or 2 carbon atoms and from 1 to 5 halogen atoms or halogenoalkylsulphonyl having 1 or 2 carbon atoms and from 1 to 5 halogen atoms.

Particular preference is given to phenethylamines of the formula (I*), in which $R^1$, $R^2$, $R^3$, $R^4$ and $R^5$ independently of one another are hydrogen, fluorine, chlorine, cyano, nitro, methyl, ethyl, n- or i-propyl, methoxy, methylthio, methylsulphinyl, methylsulphonyl, dimethylamino, trifluoromethyl, trifluoromethoxy, difluoromethoxy, trifluoromethylthio, difluoromethylthio, trifluoromethylsulphinyl, difluoromethylsulphinyl, trifluoromethylsulphonyl or difluoromethylsulphonyl.

A very particularly preferred group of optically active phenethylamines are substances of the formula (I*) in which $R^4$ and $R^5$ are hydrogen, and $R^1$, $R^2$ and $R^3$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^1$ and $R^5$ are hydrogen, and $R^2$, $R^3$ and $R^4$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^3$, $R^4$ and $R^5$ are hydrogen, and $R^1$ and $R^2$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^1$, $R^4$ and $R^5$ are hydrogen, and $R^2$ and $R^3$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^2$, $R^4$ and $R^5$ are hydrogen, and $R^1$ and $R^3$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^2$, $R^3$ and $R^4$ are hydrogen, and $R^1$ and $R^5$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^1$, $R^3$ and $R^5$ are hydrogen, and $R^2$ and $R^4$ independently of one another are fluorine, chlorine, nitro, methyl, methoxy, methylthio, methylsulphinyl or methylsulphonyl.

Another very particularly preferred group of optically active phenethylamines are substances of the formula (I*) in which $R^2$, $R^3$, $R^4$ and $R^5$ are hydrogen, and $R^1$ is fluorine, chlorine, nitro, methyl, methoxy, methylthio, methylsulphinyl or methylsulphonyl.

Another very particularly preferred group of optically active phenethylamines are substances of the formula (I*) in which $R^1$, $R^3$, $R^4$ and $R^5$ are hydrogen, and $R^2$ is fluorine, chlorine, nitro, methyl, methoxy, methylthio, methylsulphinyl or methylsulphonyl.

Another very particularly preferred group of optically active phenethylamines are substances of the formula (I*) in which $R^1$, $R^2$, $R^4$ and $R^5$ are hydrogen, and $R^3$ is fluorine, chlorine, nitro, methyl, methoxy, methylthio, methylsulphinyl or methylsulphonyl.

The optically active phenethylamines of the formula (I*) are known or can be prepared by known methods (cf. DE-A 43 32 738).

The acetophenone derivatives required as reaction components for carrying out the process according to the invention are generally defined by the formula (II). In each case, those acetophenone derivatives in which the substituents $R^1$, $R^2$, $R^3$, $R^4$ and $R^5$ are as defined for the corresponding substituents in the optically active phenethylamines of the formula (I*) are used.

Preference is given to acetophenone derivatives of the formula (II) in which $R^1$, $R^2$, $R^3$, $R^4$ and $R^5$ independently of one another are hydrogen, fluorine, chlorine, bromine, cyano, nitro, alkyl having from 1 to 4 carbon atoms, alkoxy having 1 or 2 carbon atoms, alkylthio having 1 or 2 carbon atoms, alkylsulphinyl having 1 or 2 carbon atoms, alkylsulphonyl having 1 or 2 carbon atoms, dialkylamino having in each case 1 or 2 carbon atoms in the alkyl chains, halogenoalkyl having 1 or 2 carbon atoms and from 1 to 5 halogen atoms, halogenoalkoxy having 1 or 2 carbon atoms and from 1 to 5 halogen atoms, halogenoalkylthio having 1 or 2 carbon atoms and from 1 to 5 halogen atoms, halogenoalkylsulphinyl having 1 or 2 carbon atoms and from 1 to 5 halogen atoms or halogenoalkylsulphonyl having 1 or 2 carbon atoms and from 1 to 5 halogen atoms.

Particular preference is given to acetophenone derivatives of the formula (II) in which $R^1$, $R^2$, $R^3$, $R^4$ and $R^5$ independently of one another are hydrogen, fluorine, chlorine, cyano, nitro, methyl, ethyl, n- or i-propyl, methoxy, methylthio, methylsulphinyl, methylsulphonyl, dimethylamino, trifluoromethyl, trifluoromethoxy, difluoromethoxy, trifluoromethylthio, difluoromethylthio, trifluoromethylsulphinyl, difluoromethylsulphinyl, trifluoromethylsulphonyl or difluoromethylsulphonyl.

A particularly preferred group of acetophenone derivatives are substances of the formula (II) in which $R^4$ and $R^5$ are hydrogen, and $R^1$, $R^2$ and $R^3$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^1$ and $R^5$ are hydrogen, and $R^2$, $R^3$ and $R^4$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^3$, $R^4$ and $R^5$ are hydrogen, and $R^1$ and $R^2$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^1$, $R^4$ and $R^5$ are hydrogen, and $R^2$ and $R^3$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^2$, $R^4$ and $R^5$ are hydrogen, and $R^1$ and $R^3$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^2$, $R^3$ and $R^4$ are hydrogen, and $R^1$ and $R^5$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^1$, $R^3$ and $R^5$ are hydrogen, and $R^2$ and $R^4$ independently of one another are fluorine, chlorine, nitro, methyl, methoxy, methylthio, methylsulphinyl or methylsulphonyl.

Another very particularly preferred group of acetophenone derivatives are substances of the formula (II) in which $R^2$, $R^3$, $R^4$ and $R^5$ are hydrogen, and $R^1$ is fluorine, chlorine, nitro, methyl, methoxy, methylthio, methylsulphinyl or methylsulphonyl.

Another very particularly preferred group of acetophenone derivatives are substances of the formula (II) in which $R^1$, $R^3$, $R^4$ and $R^5$ are hydrogen, and $R^2$ is fluorine, chlorine, nitro, methyl, methoxy, methylthio, methylsulphinyl or methylsulphonyl.

Another very particularly preferred group of acetophenone derivatives are substances of the formula (II) in which $R^1$, $R^2$, $R^4$ and $R^5$ are hydrogen, and $R^3$ is fluorine, chlorine, nitro, methyl, methoxy, methylthio, methylsulphinyl or methylsulphonyl.

The acetophenone derivatives of the formula (II) are known or can be prepared by known methods.

Suitable diluents for carrying out the first stage of the process according to the invention are all inert organic solvents. Preference is given to aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, tetrachloromethane, dichloroethane or trichloroethane; nitriles, such as n- or i-butyronitrile or benzonitrile.

A suitable catalyst for the first stage of the process according to the invention are all acidic reaction accelerators suitable for reactions of this type. Preference is given to inorganic or organic protic or Lewis acids and also polymeric acids, such as, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, titanium tetrachloride, tetrabutyl orthotitanate, zinc chloride, iron(III) chloride, antimony pentachloride, acidic ion exchangers, acidic aluminas and acidic silica gel.

The reaction temperatures for the first stage of the process according to the invention can be varied within a relatively large range. In general, temperatures between 20° C. and 200° C., preferably between 20° C. and 150° C., are used.

Both the first and also the second and third stages of the process according to the invention are generally carried out under atmospheric pressure. It is, however, also possible to work under increased or reduced pressure, generally between 0.1 and 10 bar.

The first stage of the process according to the invention is generally carried out using, per mol of optically active phenethylamine of the formula (I*), from 0.5 to 5 mol, preferably from 0.8 to 2 mol, of acetophenone derivative of the formula (II) and optionally a small amount, generally between $10^{-3}$ and $10^{-5}$ mol of catalyst. In detail, the procedure generally involves dissolving the starting materials in a diluent which is not very miscible with water, then adding the catalyst and heating to boiling. The water formed during the reaction is generally distilled off azeotropically and optionally collected in a water separator. The reaction products are generally isolated by firstly filtering the reaction mixture and then evaporating it under reduced pressure. The resulting product is generally sufficiently pure for further reaction. It can, however, also be freed from contaminants still present using customary purification methods, such as, for example, by chromatography or recrystallization.

Suitable racemization reagents for the second stage of the process according to the invention are all customary metal hydroxides which have a water content between 0.1 and 50% by weight, preferably between 0.1 and 30% by weight. Preference is given to alkali metal or alkaline earth metal hydroxides, such as sodium hydroxide, potassium hydroxide, calcium hydroxide or magnesium hydroxide. The water content can, where appropriate, be adjusted by adding water.

The reaction temperatures in the second stage of the process according to the invention can also be varied within a relatively large range. Temperatures between 50° C. and 250° C., preferably between 80° C. and 180° C., are generally used.

The second stage of the process according to the invention is generally carried out under a protective-gas atmosphere. Suitable and preferred protective gases are inert gases, such as nitrogen or argon.

The second stage of the process according to the invention is generally carried out using, per mol of optically active Schiff base of the formula (III*), from 1 to 10 mol, preferably from 1 to 5 mol. of metal hydroxide, with the addition, where appropriate, of additional water. In detail, the procedure generally involves heating the reaction mixture to the desired temperature, optionally under a protective-gas atmosphere, then cooling it and working it up in the usual manner. A preferred variant, however, involves adding to the cooled reaction mixture an amount of acid sufficient to give a strongly acidic mixture, which can be used directly in the third stage.

Suitable acids for cleaving the Schiff bases of the formula (III) in the third stage of the process according to the invention are all customary inorganic or organic acids or else acidic polymers, in each case in the presence of water. Preference is given to hydrochloric acid, sulphuric acid, phosphoric acid, formic acid, acetic acid, trifluoroacetic acid, methanesulphonic acid, trifluoromethanesulphonic acid, toluenesulphonic acid or acidic ion exchangers.

The reaction temperatures in the third stage of the process according to the invention can also be varied within a relatively large range. Temperatures between 20° C. and 150° C., preferably between 20° C. and 120° C., are generally used.

The third stage of the process according to the invention is generally carried out using, per mol of Schiff base of the formula (III), an excess of acid and also water. The procedure preferably involves adding aqueous acid or water and acid to the mixture produced in the second stage without prior isolation of the racemic Schiff base, and heating the resulting mixture to the desired temperature until the reaction is complete.

The mixture is worked up by customary methods. This generally involves extracting the reaction mixture with a solvent which is not very miscible with water, drying the organic phase and then evaporating it under reduced pressure. The acetophenone derivative which remains may, optionally after prior purification, be reused in the first stage of the process according to the invention. The aqueous phase which remains following extraction is generally worked up by firstly adding aqueous alkaline solution in order to render it basic, extracting the resulting mixture with an organic solvent which is not very miscible with water, drying the organic phase and evaporating it under reduced pressure. The resulting product can be freed from contaminants still present by customary methods, such as distillation, crystallization or chromatography.

The racemic phenethylamines of the formula (I) obtainable by the process according to the invention can be used either directly or following prior racemate resolution as intermediates for further syntheses. In particular, (R)-phenethylmines of the formula (I) are useful intermediates in the preparation of pharmaceuticals or of active ingredients having insecticidal, fungicidal or herbicidal properties (cf. EP-A 0 519 211, EP-A 0 453 137, EP-A 0 283 879, EP-A 0 264 217 and EP-A 0 341 475).

Thus, for example, from racemic 1-(4-chlorophenyl)-ethylamine, it is possible to obtain the (R)-enantiomer by mixing a solution of the racemate in ethanol and a solution of (S)-(-)-N-phenylcarbamate lactic acid in ethanol at temperatures between 60° C. and 70° C., filtering off the resulting crystal sludge with suction and treating it with aqueous sodium hydroxide solution in the presence of methylene chloride (cf. EP-A 0 341 475). From the (R)-1-(4-chlorophenyl)-ethylamine, it is possible to prepare the fungicidally active diastereomeric mixture of N-(R)-[1-(4-chlorophenyl)-ethyl]-(1R)-2,2-dichloro-1-ethyl-3t-methyl- 1r-cyclopropane-carboxamide and N-(R)-[1-(4-chlorophenyl)-ethyl]-(1S)-2,2-dichloro-1-ethyl-3t-methyl-1r-cyclopropane-carboxamide of the formulae

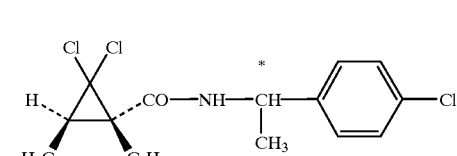
(IV-a)

and

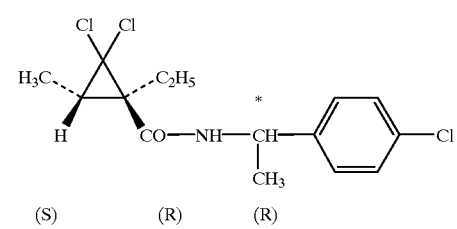
(IV-b)

by reacting a 1:1 mixture of (1R)-2,2-dichloro-1-ethyl-3t-methyl-1r-cyclopropane-carbonyl chloride and (1S)-2,2-dichloro-1-ethyl-3t-methyl-1r-cyclopropane-carbonyl chloride of the formulae

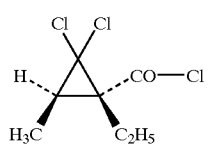
(Va)

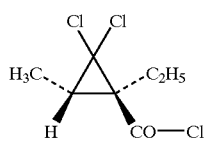
(Vb)

with R-1-(4-chlorophenyl)-ethylamine of the formula

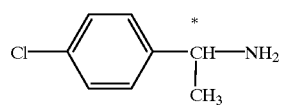
(I-1)

in the presence of a diluent, such as methyl chloride, and in the presence of an acid-binding agent, such as triethylamine.

The process according to the invention is illustrated by the following examples.

PREPARATION EXAMPLES

EXAMPLE 1

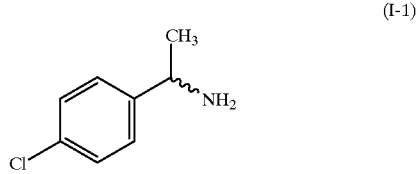
(I-1)

First Stage:

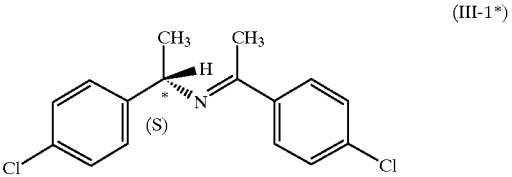
(III-1*)

8 g of tetrabutyl ortho-titanate are added to a solution of 116 g (0.72 mol) of (S)-1-(4-chlorophenyl)-ethylamine (65% ee) and 114.5 g (0.727 mol) of 4-chloroacetophenone in 500 ml of toluene at room temperature with stirring, and the mixture is then refluxed for 6 hours at the water separator. The reaction mixture is filtered, and the filtrate is evaporated under reduced pressure to give 191.3 g (91% of theory) of (S)-[1-(4-chlorophenyl)-ethyl]-[1-(4-chlorophenyl)-ethylidene]-amine.

$^1$H-NMR (CDCl$_3$,TMS, 300 MHz): δ=1.48 (d, 3H); 2.24 (s, 3H); 4.72 (q, 1H), 7.18–7.45 (m, 8H) ppm Second and Third Stage:

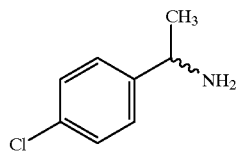
(I-1)

A mixture of 89 g (0.3 mol) of (S)-[1-(4-chlorophenyl)-ethyl]-[1-(4-chlorophenyl)-ethylidene]-amine (65% ee) and 39.6 g (0.7 mol) of potassium hydroxide having a water content of 15% by weight is heated to from 130 to 160° C. with stirring for 16 hours. The reaction mixture is then cooled, 100 ml of 2 normal aqueous sulphuric acid are added, and the mixture is refluxed for 2 hours.

The mixture is cooled to room temperature and extracted three times with dichloromethane.

The aqueous phase is rendered alkaline using concentrated, aqueous sodium hydroxide solution with cooling. The resulting mixture is extracted three times with dichloromethane. The combined organic phases are dried over sodium sulphate and then evaporated under reduced pressure. This gives 39.4 g of a product which, according to gas-chromatographic analysis, consists of 96.3% of racemic 1-(4-chlorophenyl)-ethylamine. Thus, the calculated yield is 84% of theory.

Example 2

Second and Third stage:

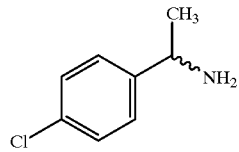
(I-1)

6.1 g of water are added to a mixture of 89 g (0.3 mol) of (S)-[1-(4-chlorophenyl)-ethyl]-[1-(4-chlorophenyl)-ethylidene]-amine (65% ee) and 39.6 g (0.7 mol) of potassium hydroxide having a water content of 15% by weight, and the mixture is heated to from 130 to 160° C. with stirring for 16 hours. The reaction mixture is then cooled, 100 ml of 2 normal aqueous sulphuric acid are added, and the mixture is refluxed for 2 hours. The mixture is cooled to room temperature and extracted three times with dichloromethane.

The aqueous phase is rendered alkaline using concentrated, aqueous sodium hydroxide solution with cooling. The resulting mixture is extracted three times with dichloromethane. The combined organic phases are dried over sodium sulphate and then evaporated under reduced pressure. This gives 38.1 g of a product which, according to gas-chromatographic analysis, consists of 95.7% of racemic 1-(4-chlorophenyl)-ethylamine. Thus, the calculated yield is 82% of theory.

Example 3

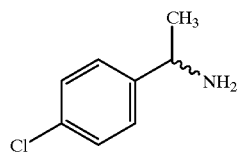
(I-1)

First Stage:

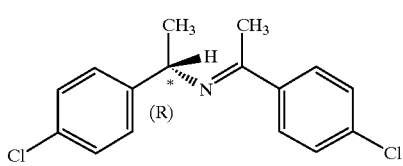
(III-2*)

3 g of tetrabutyl ortho-titanate are added to a solution of 52 g (0.35 mol) of (R)-1-(4-chlorophenyl)-ethylamine (97% ee) and 51.7 g (0.353 mol) of 4-chloroacetophenone in 300 ml of toluene at room temperature with stirring, and then the mixture is refluxed for 2 hours at the water separator. A further 2 g of tetrabutyl ortho-titanate are added, and the mixture is refluxed for a further 6 hours. A further 2 g of tetrabutyl ortho-titanate are then added, and the mixture is then refluxed for 3 hours. The reaction mixture is then filtered. The filtrate is evaporated under reduced pressure to give 67.3 g (66% of theory) of (R)-[1-(4-chlorophenyl)-ethyl]-[1-(4-chlorophenyl)-ethylidene]-amine.

$^1$H-NMR (CDCl$_3$, TMS, 300 MHz): δ=1.48 (d, 3H); 2.24 (s, 3H); 4.72 (q, 1H), 7.18–7.45 (m, 8H) ppm Second and Third Stage:

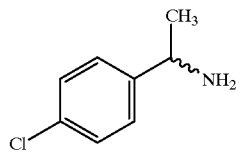
(I-1)

A mixture of 9.6 g (0.026 mol) of (R)-[1-(4-chlorophenyl)-ethyl]-[1-(4-chlorophenyl)-ethylidene]-amine (97% ee) and 4.22 g (0.075 mol) of potassium hydroxide having a water content of 15% by weight is heated to from 150 to 160° C. with stirring for 20 hours. The reaction mixture is then cooled, 35 ml of 2 normal aqueous sulphuric acid are added, and the mixture is refluxed for 4 hours. The mixture is cooled to room temperature and extracted three times with dichloromethane.

The aqueous phase is rendered alkaline using concentrated, aqueous sodium hydroxide solution with cooling. The resulting mixture is extracted three times with dichloromethane. The combined organic phases are dried over sodium sulphate and then evaporated under reduced pressure. This gives 3.7 g of a product which, according to gas-chromatographic analysis, consists of 97% of racemic 1-(4-chlorophenyl)-ethylamine. Thus, the calculated yield is 87% of theory.

COMPARATIVE EXAMPLE A

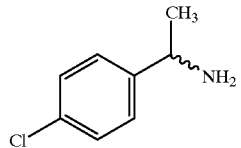
(I-1)

First Stage:

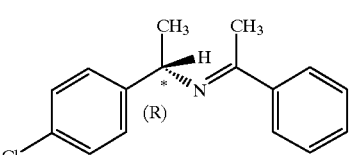
(III-3*)

0.3 g of zinc chloride is added to a solution of 20 g (0.128 mol) of (R)-1-(4-chlorophenyl)-ethylamine (97% ee) and 15.6 g (0.13 mol) of acetophenone in 70 ml of toluene at room temperature with stirring, and the mixture is then refluxed for 74 hours at the water separator. The reaction mixture is then filtered. The filtrate is evaporated under reduced pressure to give 15.56 g (47% of theory) of (R)-[1-(4-chlorophenyl)-ethyl]-[1-phenyl-ethylidene]-amine.

Second and Third Stage:

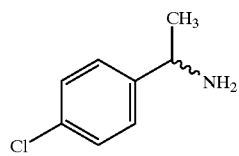
(I-1)

A mixture of 6.2 g of (R)-[1-(4-chlorophenyl)-ethyl]-[1-phenyl-ethylidene]-amine (97% ee) and 0.75 g of potassium tert-butoxide is heated to 110° C. with stirring under an argon atmosphere for 6 hours. The reaction mixture is then cooled to room temperature, 17 ml of 2 normal aqueous sulphuric acid are added, and the mixture is refluxed for 1.5 hours. The mixture is cooled to room temperature and extracted twice with dichloromethane.

The aqueous phase is rendered alkaline using 10% strength, aqueous sodium hydroxide solution with cooling. The resulting mixture is extracted three times with dichloromethane. The combined organic phases are dried over sodium sulphate and then evaporated under reduced pressure. This gives 2.1 g of a product which, according to gas-chromatographic analysis, consists of 61.64% of racemic 1-(4-chlorophenyl)-ethylamine. Thus, the calculated yield is 36% of theory.

COMPARATIVE EXAMPLE B

Second and Third Stage:

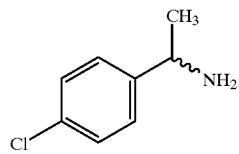
(I-1)

0.2 g of water is added to a mixture of 3.54 g (0.01 mol) of (S)-[1-(4-chlorophenyl)-ethyl]-[1-(4-chlorophenyl)-ethylidene]-amine (63.5% ee) and 0.66 g (0.01 mol) of potassium hydroxide having a water content of 15% by weight, and the mixture is heated to 130° C. with stirring for 20 hours. The reaction mixture is then cooled, 40 ml of 2 normal aqueous sulphuric acid are added, and the mixture is refluxed for 3 hours. The mixture is cooled to room temperature and extracted twice with dichloromethane.

The aqueous phase is rendered alkaline using concentrated, aqueous sodium hydroxide solution with cooling. The resulting mixture is extracted three times with dichloromethane. The combined organic phases are dried over sodium sulphate and then evaporated under reduced pressure. This gives 1.45 g of a product which, according to gas-chromatographic analysis, consists of 98.3% of (S)-1-(4-chlorophenyl)-ethylamine (ee value 64.15%).

I claim:

1. Process for the preparation of racemic phenethylamines of the formula

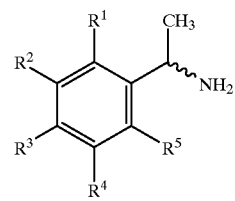
(I)

in which $R^1$, $R^2$, $R^3$, $R^4$ and $R^5$ independently of one another are hydrogen, halogen, cyano, nitro, alkyl, alkoxy, alkylthio, alkylsulphinyl, alkylsulphonyl, dialkylamino, halogenoalkyl, halogenoalkoxy, halogenoalkylthio, halogenoalkylsulphinyl or halogenoalkylsulphonyl, characterized in that a) in a first stage, optically active phenethylamines of the formula

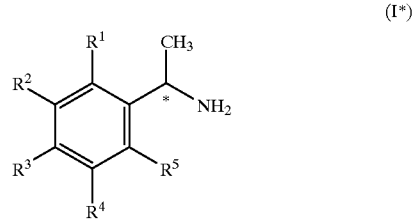
(I*)

in which
$R^1$, $R^2$, $R^3$, $R^4$ and $R^5$ are as defined above,
are reacted with acetophenone derivatives of the formula

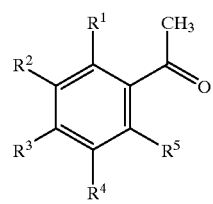
(II)

in which
$R^1$, $R^2$, $R^3$, $R^4$ and $R^5$ are as defined above,
the optically active phenethylamine used and the acetophenone derivative used each being identically substituted in the phenyl moiety,
optionally in the presence of a diluent and optionally in the presence of a catalyst, b) then in a second stage, the resulting optically active Schiff bases of the formula

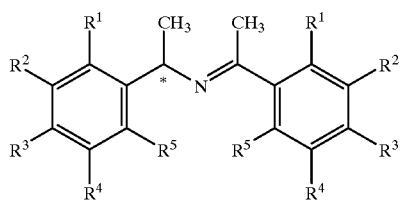

in which
R¹, R², R³, R⁴ and R⁵ are as defined above,
are reacted with metal hydroxides having a water content of between 0.1 and 50% by weight, optionally under a protective-gas atmosphere, and
c) in a third stage, the resulting racemic Schiff bases of the formula

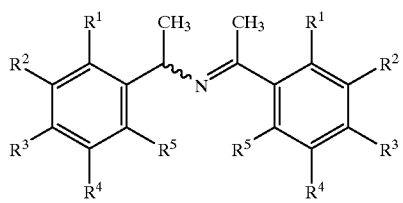

in which
R¹, R², R³, R⁴ and R⁵ are as defined above,
are reacted with acids in the presence of water.

2. Process according to claim 1, characterized in that the starting materials used are optically active phenethylamines of the formula (I*) in which R¹, R², R³, R⁴ and R⁵ independently of one another are hydrogen, fluorine, chlorine, bromine, cyano, nitro, alkyl having from 1 to 4 carbon atoms, alkoxy having 1 or 2 carbon atoms, alkylthio having 1 or 2 carbon atoms, alkylsulphinyl having 1 or 2 carbon atoms, alkylsulphonyl having 1 or 2 carbon atoms, dialkylamino having in each case 1 or 2 carbon atoms in the alkyl chains, halogenoalkyl having 1 or 2 carbon atoms and from 1 to 5 halogen atoms, halogenoalkoxy having 1 or 2 carbon atoms and from 1 to 5 halogen atoms, halogenoalkylthio having 1 or 2 carbon atoms and from 1 to 5 halogen atoms, halogenoalkylsulphinyl having 1 or 2 carbon atoms and from 1 to 5 halogen atoms or halogenoalkylsulphonyl having 1 or 2 carbon atoms and from 1 to 5 halogen atoms.

3. Process according to claim 1, characterized in that the first stage is carried out using, as reaction components, acetophenone derivatives of the formula (II) in which R¹, R², R³, R⁴ and R⁵ independently of one another are hydrogen, fluorine, chlorine, bromine, cyano, nitro, alkyl having from 1 to 4 carbon atoms, alkoxy having 1 or 2 carbon atoms, alkylthio having 1 or 2 carbon atoms, alkylsulphinyl having 1 or 2 carbon atoms, alkylsulphonyl having 1 or 2 carbon atoms, dialkylamino having in each case 1 or 2 carbon atoms in the alkyl chains, halogenoalkyl having 1 or 2 carbon atoms and from 1 to 5 halogen atoms, halogenoalkoxy having 1 or 2 carbon atoms and from 1 to 5 halogen atoms, halogenoalkylthio having 1 or 2 carbon atoms and from 1 to 5 halogen atoms, halogenoalkylsulphinyl having 1 or 2 carbon atoms and from 1 to 5 halogen atoms or halogenoalkylsulphonyl having 1 or 2 carbon atoms and from 1 to 5 halogen atoms.

4. Process according to claim 1, characterized in that, in the first stage, (S)-1-(4-chloro-phenyl)-ethylamine is reacted with 4-chloroacetophenone.

5. Process according to claim 1, characterized in that the first stage is carried out in the presence of an acidic catalyst.

6. Process according to claim 1, characterized in that, in the second stage, alkali metal or alkaline earth metal hydroxides having a water content of between 0.1 and 30% by weight are used as racemization reagents.

7. Process according to claim 1, characterized in that the acids used in the third stage are inorganic or organic acids or acidic polymers, each in the presence of water.

8. Process according to claim 1, characterized in that the first stage is carried out at temperatures between 20° C. and 200° C., the second stage is carried out at temperatures between 50° C. and 250° C., and the third stage is carried out at temperatures between 20° C. and 150° C.

* * * * *